United States Patent [19]

Mildenberger et al.

[11] 4,110,336
[45] Aug. 29, 1978

[54] MONO-, DI- AND TRI-ESTERS OF THIOPHOSPHONIC ACID AND THEIR USE AS PESTICIDES

[75] Inventors: Hilmar Mildenberger, Kelkheim, Taunus; Gerhard Stähler, Frankfurt am Main; Ludwig Emmel, Bergen-Enkheim, all of Germany

[73] Assignee: Hoechst Aktiengesellschaft, Frankfurt am Main, Germany

[21] Appl. No.: 816,968

[22] Filed: Jul. 19, 1977

Related U.S. Application Data

[63] Continuation of Ser. No. 411,748, Nov. 1, 1973, abandoned.

[30] Foreign Application Priority Data

Nov. 4, 1972 [DE] Fed. Rep. of Germany ....... 2254042

[51] Int. Cl.² .............................................. C07F 9/40
[52] U.S. Cl. ................................. 260/307 G; 424/200
[58] Field of Search .................................... 260/307 G

[56] References Cited

U.S. PATENT DOCUMENTS 3,709,902  1/1973  Boyce et al. .................... 260/307 G
3,711,494  1/1973  Adolphi et al. ................. 260/307 G

FOREIGN PATENT DOCUMENTS 1,963,672  6/1971  Fed. Rep. of Germany.
1,213,707  11/1970  United Kingdom.

Primary Examiner—Raymond V. Rush
Attorney, Agent, or Firm—Curtis, Morris & Safford

[57] ABSTRACT

Compounds having the formula

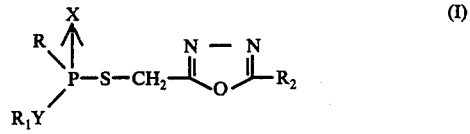
(I)

in which R is alkyl, haloalkyl, cycloalkyl, cycloalkenyl, phenyl, optionally substituted by chlorine, methyl or methoxy, moreover bicycloheptyl or bicycloheptenyl; $R_1$ is alkyl, optionally substituted by halogen, nitro, cyano or a radical having the formula

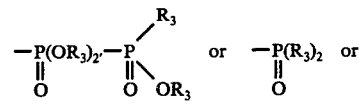

alkenyl, optionally substituted by halogen; alkinyl, alkoxyalkyl, alkylmercapto-alkyl, cycloalkyl, phenyl, halophenyl, trifluoromethylphenyl, benzyl or a radical having the formula

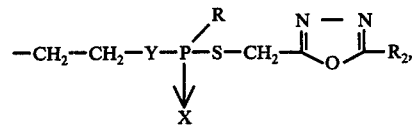

$R_2$ is alkyl, alkoxyalkyl, phenyl or halophenyl, $R_3$ is methyl or ethyl, and X and Y are oxygen or sulfur are valuable pesticides.

4 Claims, No Drawings

MONO-, DI- AND TRI-ESTERS OF THIOPHOSPHONIC ACID AND THEIR USE AS PESTICIDES

This is a continuation of application Ser. No. 411,748, filed Nov. 1, 1973, and now abandoned.

Subject of the present invention are monoesters, diesters and triesters of thiophosphonic acid having the general formula

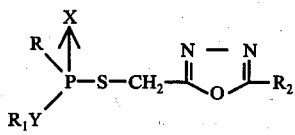

in which
R is $(C_1-C_4)$ alkyl, $(C_1-C_4)$ haloalkyl, $(C_5-C_6)$ cycloalkyl, $(C_5-C_6)$ cycloalkenyl, phenyl, optionally substituted by chlorine, methyl or methoxy, moreover bicycloheptyl or bicycloheptenyl;

$R_1$ is $(C_1-C_{12})$ alkyl, optionally substituted by halogen, nitro, cyano or a radical having the formula

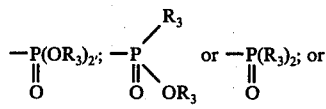

$(C_3-C_4)$ alkenyl, optionally substituted by halogen; $(C_3)$ alkinyl; $(C_2-C_6)$ alkoxyalkyl; $(C_1-C_3)$ alkylmercaptoalkyl; $(C_5-C_6)$ cycloalkyl; phenyl; halophenyl; trifluoromethylphenyl; benzyl or a radical having the formula

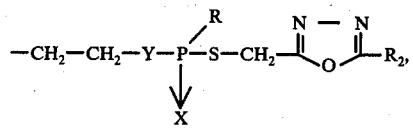

$R_2$ is $(C_1-C_4)$ alkyl, $(C_2-C_4)$ alkoxyalkyl, phenyl or halophenyl, $R_3$ is methyl or ethyl, and X and Y are oxygen or sulfur.

Besides the meanings specified in the examples, the symbols R, $R_1$ and $R_2$ may preferably have the following meanings:

R: isopropyl, sec. butyl, β-chloroethyl, cyclopentyl, 2-, 3-, or 4- chlorophenyl, 2,4-, 3,4-, 3,5- or 2,6-dichlorophenyl; 2- or 4-methylphenyl, 4-ethylphenyl; 2.2.1-bicycloheptyl-(2);

$R_1$: n-pentyl, n-hexyl; 2,2.2-trichloroethyl, 2,3-dibromopropyl, crotyl; cyclopentyl; 2-, 3- or 4-bromophenyl, 2,3-, 2,6-, or 3,5-dichlorophenyl or dibromophenyl;

$R_2$: ethyl, methoxymethyl, 3-methoxypropyl, 2-ethoxyethyl; phenyl; 2- or 4-chlorophenyl, 2,4- or 2,6-dichlorophenyl, 2-, 3- or 4-bromophenyl.

The compounds of the formula I are prepared by reacting compounds having the formula

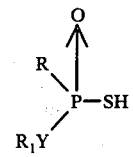

or their salts, if necessary in the presence of an acid-binding agent, with 2-halogenomethyl-1,3,4-oxdiazoles having the formula

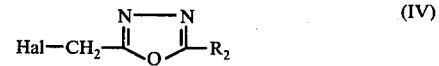

in which
Hal represents preferably chlorine or bromine.

As salts of compounds having the formula III the alkaline metal salts, alkaline earth metal salts or ammonium salts or salts of organic bases are especially used. In case that the free compounds are used, acid-binding agents must be added, such as alkali metal hydroxides, alcoholates or carbonates, ammonia or tert. nitrogen bases such as triethylamine, dimethylaniline, pyridine, or quinoline.

Generally, the compounds having the formula III are used in slightly excessive quantities of up to 10%. In principle it is possible to use excess halogenomethyloxdiazole, as well but neither technically nor economically is there any advantage.

The reaction is performed in a temperature range between room temperature and the decomposition temperature of the final products, respectively the temperature at which secondary reactions between excess starting material and the reaction end product may occur i.e. between 20° and 100° C, preferably between 30° C and 80° C. The reaction, being mostly exothermic, can be carried through without solvents. However, in order to guarantee a better temperature control, the reaction is generally performed in solvents inert to respect to the starting materials. As solvents are suitable, besides the reaction products themselves, especially low aliphatic alcohols having from 1-4 carbon atoms, low aliphatic ketones such as, for instance, acetone or methyl ethyl ketone, short chain aliphatic nitriles, ethers such as, for example, tetrahydrofurane or glycol dimethyl ether, amides of low aliphatic carboxylic acids such as dimethyl formamide or dimethyl acetamide or water when water-soluble starting materials are used. In some cases it may also be advantageous to use aromatic hydrocarbons or chlorinated aliphatic hydrocarbons with or without small quantities of the above mentioned solvents as solubilizers.

The process may be performed by various methods which are principally known, such as are described, for example, in the general preparation methods A-D of the Examples. The 2-halogen-1,3,4-oxdiazoles used for this purpose may be prepared according to Elderfield "Heterocyclic compounds", Vol. 7, pg. 526-527 by splitting off water from corresponding 1-halogenacetyl-2-acylhydrazides or according to German "Offenlegungsschrift" 2.047.464 and 2.047.465 from corresponding acylhydrazides with haloacetic acids in the presence of phosphorus halides. The dithiophosphonic acid anhydrides used for this purpose, being partially unknown, may be obtained according to the general process described in Houben-Weyl, 4th edition vol.XX-I/1, pg. 616.

The compounds claimed by the present invention are efficient insecticidal, acaricidal and nematocidal agents.

They act as contact as well as stomach poisons. Moreover, they show excellent systemic properties, being equally well absorbed by the roots of the plants and by the above-ground growing parts.

Because of their properties and their good tolerability to plants they are useful for combating numerous insect pests on crop plants.

They can be used successfully against both sucking and biting insects, for example, against members of the following classes or families:

| | |
|---|---|
| Tettigonioideae | Bruchidae |
| Acridoideae | Curculionidae |
| Gryllidae | Bostrychidae |
| Gryllotalpidae | Carabidae |
| Blattidae | Cassidinae |
| Reduviidae | Tineidae |
| Pyrrhocoriae | Noctuidae |
| Cimicidae | Lymantriidae |
| Pentatomidae | Pyralidae |
| Delphacidae | Geometridae |
| Cicadellidae | Hyponomoitidae |
| Aphidoideae | Pioridae |
| Psylloideae | Tortricidae |
| Aleurodidae | Culicidae |
| Diaspididae | Tipulidae |
| Coccidae | Stomoxydae |
| Pseudococcidae | Tabanidae |
| Scarabaeidae | Tephritidae |
| Dermestidae | Muscidae |
| Coccinellidae | Calliphorinae |
| Tenebrionidae | Cecidomyiidae |
| Chrysomelidae | Pulicidae |

The compounds act also against many types of mites (Acarinae), for example against members of the families Tetranychidae, Dermanyssidae, Tarsonemidae and Eriophyidae.

The novel compounds are furthermore useful for combating plant nematodes such as Meloidogynes spp., Heterodora spp. Ditylenchus spp., Pratylenchus spp., Paratylenchus spp., Anguina spp., Helicotylenchus spp., Tylenchorhynchus spp., Rotylenchulus spp., Tylenchulus spp., Radopholus spp., Belonolaismus spp., Trichodorus spp., Longidorus spp., Aphelenchoides spp., Xiphinema spp.

Among the pests against which the invention compounds are active are the following: beetle species such as strawberry blossom weevil (*Anthonomus rubi*), the Mexican bean beetle (*Epilachna varivestis*), the Colorado beetle (*Leptinotarsa decemlineata*), the grain weevil (*Calandra granaria*), mealworm (*Tenebrio molitor*); larvae of the codling moth (*Carpocapsa pomonella*), of the green oak leaf roller (*Tortrix viridana*), of the tortrix moth (*Capua reticulane*), of the Asiatic cotton moth (*Prodenia litura*), of the corn borer (*Ostrinia nubilalis*); aphids, such as the bean aphid (*Doralis fabae*), the green peach aphid (*Myzodes persicae*), the wooly aphid (*Eriosoma lanigerum*); cicadae such as *Nilaparvata lugens* and *Nephotettix bipunctata*; bugs sucking on plants such as cotton stainers (*Oncopeltus fasciatus* and *Dysdercus fasciatus*); locusts such as the North African variety of *Locusta migratoria*; cockroach varieties impeaching hygiene such as *Periplaneta americana* and *Phyllodromia germanica*; spider mite varieties such as *Tetranychus urticae* and *Metatetranychus ulmi*.

Due to the systemic properties of the compounds well hidden noxious insects can be combated, too, for example aphids living inside galls such as the mealy apple aphid (*Yezabura communis*) and *Anuraphis roseus*.

The excellent root-systemic properties of the compounds allow for their use as insecticidal and acaricidal granules, so that the protection of the growing young plants against the actions of aphids, spider mites, larvae etc. is guaranteed for weeks if the granules are dispersed simultaneously with the seed, such as cotton, broad beans etc.

Therefore, subject of the invention are also pesticidal agents which contain as active agent compounds having the formula I. For this purpose, the compounds having the general formula I may be formulated in the usual admixtures with solid or liquid inert carrier substances, adhesives, wetting and dispersing agents, or grinding auxiliaries, as wettable powders, emulsion concentrates, granules etc.

As carrier material, mineral substances may be used, such as aluminium silicates, argillaceous earths, kaolin, chalks, siliceous chalks, talcum, kieselguhr or hydrated silicic acids, or preparations of these mineral substances with special additives, for example chalk with sodium stearate. As carrier material for liquid preparations, all usual and suitable organic solvents may be employed, for example toluene, xylene, diacetone alcohol, isophorone, gasolines, paraffin oils, dioxan, dimethyl formamide, dimethyl sulphoxide, ethyl acetate, butyl acetate, tetrahydrofuran, chlorobenzene and the like.

As adhesives, there may be used glue-like cellulose products or polyvinyl alcohols.

As wetting agents, all suitable emulsifiers may be used, such as oxethylated alkylphenols, salts of aryl- or alkylarylsulphonic acids, salts of ethoxylated benzenesulphonic acids, or soaps.

Suitable dispersing agents are cellulose pitch (salts of sulphite waste liquors), salts of naphthalenesulphonic acid or, in certain cases, hydrated silicic acids or also kieselguhr.

As grinding auxiliaries, suitable inorganic or organic salts, such as sodium sulphate, ammonium sulphate, sodium carbonate, sodium bicarbonate, sodium thiosulphate, sodium stearate, sodium acetate may be used.

The pesticidal compositions may optionally be mixed with other insecticidal, nematocidal and/or fungicidal agents. These pesticidal compositions are containing, generally, from 1 to 95% of compounds having the formula I.

The following Examples illustrate the invention.

Preparation procedure A:

According to the reaction equation $$R-PS_2 + MeOR_1 \longrightarrow$$

II

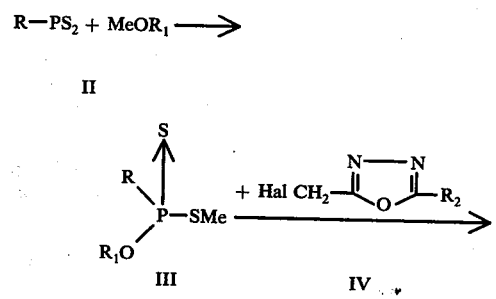

III      IV

The following compounds were prepared according to this process:

TABLE I

| Ex. No. | Reaction/product/yield/MW % of theory | reactants III | IV | phys. data | analysis in % calc. / found |
|---|---|---|---|---|---|
| 1 | (structure) 98 % $C_{10}H_{19}N_2O_2PS_2$ MW 294 | (structure) | (structure) | $n_D^{23,5}$ = 1.526 | 10,5 P 10,3 / 9,5 N 9,4 |
| 2 | (structure) 95 % $C_9H_{17}N_2O_2PS_2$ MW 280 | (structure) | (structure) | $n_D^{23,5}$ = 1.542 | 11,1 P 11,3 / 10,0 N 9,9 |
| 3 | (structure) 91 % $C_9H_{17}N_2O_2PS_2$ MW 280 | (structure) | (structure) | $N_D^{22}$ = 1.543 | 10,0 N 9,8 / 22,8 S 22,6 |
| 4 | (structure) 95 % MW 294 | (structure) | (structure) | $n_D^{22}$ = 1.539 | 9,5 N 9,5 / 21,8 S 21,8 |
| 5 | (structure) MW 294 | (structure) | (structure) | $n_D^{22}$ = 1.541 | 9,5 N 9,6 / 21,8 S 22,4 |

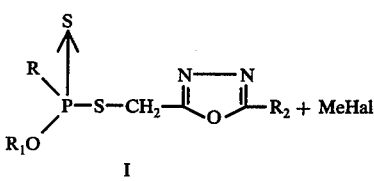

equimolar quantities of dithiophosphonic acid anhydride and of alcaline metal alcoholate II in a 5 to 10 fold quantity of alcohol were mixed together and stirred for a period of from 5 minutes to 1 hour, thus obtaining the intermediate product according to formula III. Subsequently, equimolar quantities of a 2-halogenomethyl-oxdiazole having the general formula IV were added and the whole was heated to temperatures between 20° and 80° C for a period from 10 minutes to 5 hours, depending on the reaction. For working-up, the alkali metal halide was separated by suction filtration, the solvent eliminated by distillation and the residue dissolved in another solvent immiscible with water. This solution was washed several times with water, dried and concentrated. Generally the esters were obtained as oils which cannot be distilled without decomposition occurring.

General preparation procedure B

According to the reaction equation

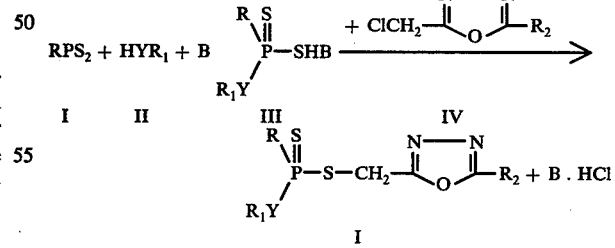

a dithiophosphonic acid anhydride I was stirred together with stoichiometric quantities of a phenol, a thiophenol, an alcohol, a glycol or mercaptan II in a solvent being inert under the reaction conditions and immiscible with water (for example $CH_2Cl_2$, toluol), heated to from 60°–110° C and reacted with the equimolar quantity of a tert. base B (for example, triethylamine, pyridine). To the intermediate product III thus prepared there was added a stoichiometric quantity of 2-halogenomethylox-diazole IV. The reaction usually took place within from 10 minutes to 5 hours at temperatures of from 20°–110° C, respectively the boiling point of the solvent used. The work-up was performed by washing out the amine-salt with water, drying the organic phase e.g. with sodium sulfate and eliminating the solvent by distillation.

The reaction products were usually obtained as oils which cannot be subjected to distillation without decomposition.

The following compounds were prepared according to method B:

TABLE II

| Ex. No. | Reaction product/yield/MW % of theory | reactants III | IV | phys. data | analysis in % calc. | analysis in % found |
|---|---|---|---|---|---|---|
| 6 | ![structure] MW 362,5 92 % | structure with (C$_2$H$_5$)$_3$N · HS– , CH$_3$, p-chlorophenoxy | oxadiazole with CH(CH$_3$)$_2$ and CH$_2$Cl | $n_D^{23,5}$ = 1.578 | P 8,55 S 17,65 | P 8,3 S 17,2 |
| 7 | ![structure] MW 462 95 % | structure with C$_4$H$_9$(n), OC$_{12}$H$_{25}$(n) | oxadiazole with CH(CH$_3$)$_2$ and CH$_2$Cl | $n_D^{23,5}$ = 1.503 | P 6,7 S 13,85 | P 6,4 S 13,6 |
| 8 | ![structure] MW 352 98 % | structure with C$_4$H$_9$(n), SC$_3$H$_7$ | oxadiazole with CH(CH$_3$)$_2$ and CH$_2$Cl | $n_D^{23,5}$ = 1.555 | P 8,8 S 27,3 | P 8,6 S 27,1 |
| 9 | ![structure] MW 449 97 % | structure with CH$_2$–CH(CH$_3$)$_2$ and p-bromophenoxy | oxadiazole with CH(CH$_3$)$_2$ and CH$_2$Cl | $n_D^{23,5}$ = 1.576 | P 6,9 N 6,24 | P 6,6 N 6,11 |
| 10 | ![structure] MW 484,5 77 % | structure with CH$_2$–CH(CH$_3$)$_2$, O–CH(CCl$_3$)CH$_2$NO$_2$ | oxadiazole with CH(CH$_3$)$_2$ and CH$_2$Cl | dark oil | P 6,4 Cl 22,0 | P 6,3 Cl 21,7 |

TABLE II-continued

| Ex. No. | Reaction product/yield/MW % of theory | reactants III | reactants IV | phys. data | analysis in % calc. | analysis in % found |
|---|---|---|---|---|---|---|
| 11 | ![product structure with pyrazole-oxazoline, CH₂-S-P(S)(CH₃)-O-CH(CHCl₂)-CCl=CCl₂] <br> 98% MW 478,5 | (C₂H₅)₃N · HS-P(S)(CH₃)-O-CH(CHCl₃)-CCl=CCl₂ | CH₃-CH(CH₃)- with N=N, O, CH₂Cl | $n_D^{21} = 1.5662$ | P 6,45 <br> Cl 37,0 | P 6,3 <br> Cl 37,2 |
| 12 | ![product] <br> n-C₄H₉ ring, CH₂-S-P(S)(C₂H₅)-O-C₆H₅ <br> 90% MW 356 | (C₂H₅)₃N · HS-P(S)(C₂H₅)-O-C₆H₅ | n-C₄H₉ with N=N, O, CH₂Cl | $n_D^{21} = 1.5418$ | P 8,7 <br> S 18,0 | P 8,6 <br> S 17,5 |
| 13 | ![product with CF₃-phenyl] <br> 95% MW 424 | (C₂H₅)₃N · HS-P(S)(C₂H₅)-O-C₆H₄-CF₃ | n-C₄H₉ with N=N, O, CH₂Cl | $n_D^{21} = 1.514$ | P 7,3 <br> N 6,6 | P 7,5 <br> N 6,1 |
| 14 | ![product with SC₄H₉(n)] <br> 83% MW 352 | (C₂H₅)₃N · HS-P(S)(C₂H₅)-SC₄H₉(n) | n-C₄H₉ with N=N, O, CH₂Cl | $n_D^{21} = 1.5349$ | P 8,8 <br> S 27,2 | P 8,6 <br> S 26,9 |
| 15 | ![product with OCH₂-CH=CH₂] <br> 89% MW 320 | (C₂H₅)₃N · HS-P(S)(C₂H₅)-OCH₂-CH=CH₂ | n-C₄H₉ with N=N, O, CH₂Cl | $n_D^{21} = 1.5194$ | P 9,7 <br> S 20,0 | P 9,7 <br> S 19,9 |

TABLE II-continued

| Ex. No. | Reaction product/yield/MW % of theory | reactants III | reactants IV | phys. data | analysis in % calc. | analysis in % found |
|---|---|---|---|---|---|---|
| 16 | [structure with C₂H₅O—CH₂, N=N, O, CH₂—S, P, S, C₂H₅, S—(4-Cl-C₆H₄)]<br>92 %  MW 408,2 | [structure S=P(C₂H₅)(S-4-Cl-C₆H₄)]<br>(C₂H₅)₃N · HS— | [structure C₂H₅O—CH₂, N=N, O, CH₂Cl] | $n_D^{21}$ = 1.6078 | P 7,6<br>S 23,5 | P 7,6<br>S 23,5 |
| 17 | [structure with C₂H₅O—CH₂, N=N, O, CH₂—S, P, S, C₂H₅, S(CH₂)₄CCl₃]<br>81 %  MW 471,5 | [structure S=P(C₂H₅)(S(CH₂)₄CCl₃)]<br>pyridine · HS— | [structure C₂H₅O—CH₂, N=N, O, CH₂Cl] | $n_D^{21}$ = 1.5661 | P 6,66<br>S 20,3 | P 6,3<br>S 20,5 |
| 18 | [structure with CH₃, N=N, O, CH₂—S, P, S, C₃H₇, O-(2,4-Cl₂-C₆H₃)]<br>91 %  MW 397 | [structure S=P(C₃H₇)(O-4-Cl-C₆H₄)]<br>(C₂H₅)₃N · HS— | [structure CH₃, N=N, O, CH₂Cl] | $n_D^{20}$ = 1.597 | N 7,1 | N 7,4 |
| 19 | [structure with CH₃, N=N, O, CH₂—S, P, S, C₃H₇, OC₂H₄P(OCH₃)₂=O]<br>78 %  MW 388 | [structure S=P(C₃H₇)(OC₂H₄P(OCH₃)₂=O)]<br>(C₂H₅)₃N · HS— | [structure CH₃, N=N, O, CH₂Cl] | $n_D^{20}$ = 1.537 | N 6,9<br>P 15,4 | N 6,9<br>P 15,4 |
| 20 | [structure with CH₃, N=N, O, CH₂—S, P, S, C₃H₇, OCH₂—P(CH₃)₂=O]<br>40 %  MW 342 | [structure S=P(C₃H₇)(OCH₂P(CH₃)₂=O)]<br>(C₂H₅)₃N · HS— | [structure CH₃, N=N, O, CH₂Cl] | $n_D^{20}$ 1.577 | N 8,2<br>P 18,2 | N 8,5<br>P 17,5 |

TABLE II-continued

| Ex. No. | Reaction product/yield/MW % of theory | reactants III | IV | phys. data | analysis in % calc. | analysis in % found |
|---|---|---|---|---|---|---|
| 21 | [structure with C₃H₇, SC₂H₅, N-N, CH₃, O, CH₂-S, CH₂Cl]<br>86 %  MW 293 | [structure with C₃H₇, SC₂H₅]<br>(C₂H₅)₃N · HS—P | [structure with N-N, CH₃, O, CH₂Cl] | $n_D^{20}$ = 1.590 | N 9,5<br>S 32,5 | N 9,7<br>S 33,2 |
| 22 | [structure with C₃H₇, phenyl-S, N-N, CH₃, O, CH₂-S]<br>78 %  MW 344 | [structure with C₃H₇, S-phenyl]<br>(C₂H₅)₃N · HS—P | [structure with N-N, CH₃, O, CH₂Cl] | $n_D^{20}$ = 1.630 | N 8,1<br>S 27,9 | N 8,1<br>S 27,8 |
| 23 | [bis structure with C₃H₇, O-CH₂-CH₂-O, N-N, CH₃, O, CH₂-S]<br>83 %  MW 530 | [structure with C₃H₇, O-CH₂-CH₂-O, C₃H₇]<br>(C₂H₅)₃N · HS—P ... P—SH · N(C₂H₅)₃ | [structure with N-N, CH₃, O, CH₂Cl] | $n_D^{20}$ = 1.5733 | N 9,5<br>S 32,5 | N 9,7<br>S 33,2 |

General preparation procedure C

According to the reaction equation

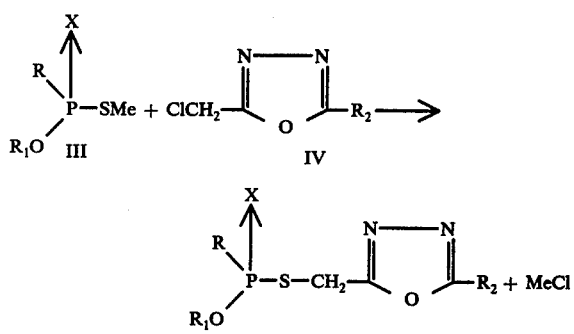

equimolar quantities of an alkali metal salt or an ammonium salt of thio- or dithiophosphonic acid monoesters III and of a 2-chloro-methyloxdiazole IV were heated to 60°–90° C for about 30 minutes in an appropriate solvent (such as for example ethanol, acetonitrile or glycol dimethyl ether). Subsequently, the solvent was eliminated by distillation, the residue taken up in a solvent immiscible with water, and worked-up in analogy to method A.

The following compounds were prepared according to this method:

TABLE III

| Ex. No. | Reaction product/yield/MW % of theory | Reactants III | Reactants IV | phys. data | analysis in % calc. found |
|---|---|---|---|---|---|
| 24 | (structure) 94%  MW 253 | (structure) | (structure) | $n_D^{20}=$ 1.566 | 11,1 N 11,2 ; 25,2 S 25,5 |
| 25 | (structure) 98%  MW 266 | (structure) | (structure) | $n_D^{20}=$ 1.549 | 11,7 P 11,5 ; 10,5 N 10,2 |
| 26 | (structure) 82%  MW 345 | (structure) | (structure) | $n_D^{20}=$ 1.562 | 18,6 S 18,9 ; 8,1 N 7,8 |
| 27 | (structure) 84%  MW 302 | (structure) | (structure) | $n_D^{20}=$ 1.532 | 10,6 S 10,3 ; 9,3 N 9,4 |
| 28 | (structure) 88%  MW 314 | (structure) | (structure) | $n_D^{20}=$ 1.539 | 10,2 S 10,1 ; 8,9 N 9,0 |
| 29 | (structure) 85%  MW 318 | (structure) | (structure) | $n_D^{20}=$ 1.563 | 20,1 S 19,5 ; 8,8 N 9,4 |
| 30 | (structure) 89%  MW 330 | (structure) | (structure) | $n_D^{20}=$ 1.562 | 8,5 N 8,0 ; 19,4 S 18,8 |

TABLE III-continued

| Ex. No. | Reaction product/yield/MW % of theory | reactants III | reactants IV | phys. data | analysis in % calc. | | found |
|---|---|---|---|---|---|---|---|
| 31 | [structure] 98 % MW 264 | [structure] | [structure CH₃—⟨N═N⟩—CH₂Cl] | $n_D^{20}=$ 1.500 | 12,1 | S | 12,0 |
| 32 | [structure Cl-phenyl] 87 % MW 266 | [structure Na-S-P] | [structure CH₃—⟨N═N⟩—CH₂Cl] | semi-solid wax | 11,7 10,5 | P N | 11,5 10,2 |

General preparation procedure D

According to the reaction equation $$RPS_2 + HOR_i + MeOH \longrightarrow \underset{II}{} \underset{III}{\overset{S}{\underset{R_1O}{R}}P-SMe} + H_2O$$

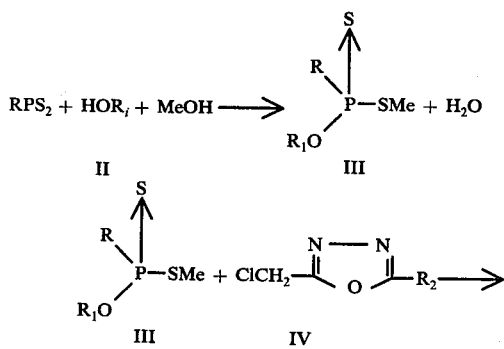

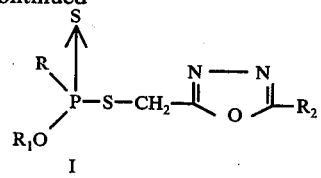

a dithiophosphonic acid anhydride was reacted with at least the stoichiometric quantity of a hydroxyl compound II. The dithiophosphonic acid monoester, formed with heat generation, was dissolved in a solution of stoichiometric quantitites of an alkali metal hydroxide in water. After having added stoichiometric quantities of a 2-chloromethyl-1,3,4-oxdiazole IV to the solution of salt III, the reaction mixture was heated to temperatures between 50°-100° C for periods from 10 minutes to 2 hours. The separated oil was taken up by an inert solvent such as methylene chloride or toluol and separated from the aqueous solution. After drying the organic phase with one of the usually used drying agents such as — for example — sodium sulfate or calcium chloride the solvent was eliminated by distillation, whereby the reaction product was generally obtained as an oil.

The following compounds were prepared according to this process:

TABLE IV

| Ex. No. | Reaction product/yield/MW % of theory | reactants | | phys. data | analysis in % calc. | | analysis in % found | |
|---|---|---|---|---|---|---|---|---|
| | | III | IV | | | | | |
| 33 | [structure] 88% MW 280 | [Na–S–P(=S)(CH₃)O–CH₂CH(CH₃)CH₃] | [oxadiazolinone–CH₂Cl] | $n_D^{20}=1.539$ | N 10.0 | S 22.9 | N 9.8 | S 22.6 |
| 34 | [structure] 85% MW 238 | [Na–S–P(=S)(CH₃)OCH₃] | [oxadiazolinone–CH₂Cl] | $n_D^{20}=1.560$ | N 11.7 | S 26.4 | N 11.4 | S 26.1 |
| 35 | [structure] 78% MW 280 | [Na–S–P(=S)(CH₃)O–CH(CH₃)C₂H₅] | [oxadiazolinone–CH₂Cl] | $n_D^{20}=1.540$ | N 10.0 | S 22.9 | N 10.1 | S 22.5 |
| 36 | [structure] 63% MW 280 | [Na–S–P(=S)(CH₃)O-n-C₄H₉] | [oxadiazolinone–CH₂Cl] | $n_D^{20}=1.542$ | N 10.0 | S 22.9 | N 9.9 | S 22.7 |
| 37 | [structure] 90% MW 306 | [Na–S–P(=S)(CH₃)O–C₆H₁₁] | [oxadiazolinone–CH₂Cl] | $n_D^{20}=1.552$ | N 9.1 | S 20.9 | N 8.9 | S 20.7 |
| 38 | [structure] 92% MW 314 | [Na–S–P(=S)(CH₃)O–CH₂–C₆H₅] | [oxadiazolinone–CH₂Cl] | $n_D^{20}=1.583$ | N 8.9 | S 20.4 | N 8.9 | S 20.1 |

TABLE IV-continued

| Ex. No. | Reaction product/yield/MW % of theory | | reactants III | IV | phys. data | analysis in % calc. | | found | |
|---|---|---|---|---|---|---|---|---|---|
| 39 | [structure with CH₃, N—N, O, CH₂—S—P(S)(C₂H₅)(OCH₃)] 78% | MW 252 | [Na—S—P(S)(C₂H₅)(OCH₃)] | [CH₃, N—N, O, CH₂Cl] | $n_D^{20}=1.556$ | 11,2 25,4 | N S | 11,0 25,1 | |
| 40 | [structure with C₃H₇] 84% | MW 266 | [Na—S—P(S)(C₃H₇)(OCH₃)] | [same] | $n_D^{20}=1.550$ | 10,5 24,0 | N S | 10,6 23,9 | |
| 41 | [structure with C₂H₅, OC₂H₄P(O)(CH₃)₂] 67% | MW 342 | [Na—S—P(S)(C₂H₅)(OC₂H₄P(O)(CH₃)₂)] | [same] | semi-solid wax | 8,2 18,7 | N S | 8,9 18,1 | |
| 42 | [structure with n-C₄H₉] 91% | MW 280 | [Na—S—P(S)(n-C₄H₉)(OCH₃)] | [same] | $n_D^{20}=1.544$ | 10,0 22,9 | N S | 9,8 23,0 | |
| 43 | [structure with CH₂—CH(CH₃)₂] 95% | M 280 | [Na—S—P(S)(CH₂CH(CH₃)₂)(OCH₃)] | [same] | $n_D^{20}=1.543$ | 10,0 22,9 | N S | 10,1 22,7 | |
| 44 | [structure with phenyl] 83% | M 300 | [Na—S—P(S)(C₆H₅)(OCH₃)] | [same] | $n_D^{20}=1.642$ | 9,3 21,3 | N S | 9,4 21,0 | |
| 45 | [structure with CH₂Cl, OC₂H₅] 94% | M 291,5 | [Na—S—P(S)(CH₂Cl)(OC₂H₅)] | [same] | $n_D^{20}=1.536$ | 12,4 9,4 | Cl N | 12,0 9,5 | |

TABLE IV-continued

| Ex. No. | Reaction product/yield/MW % of theory | reactants | | phys. data | analysis in % | | | |
|---|---|---|---|---|---|---|---|---|
| | | III | IV | | calc. | | found | |
| 46 | [structure] 86% M 320 | [structure with cyclohexyl, S, P, OC₂H₅, Na—S] | [structure CH₃, N—N, O, CH₂Cl] | $n_D^{20} = 1.582$ | 8,7 20,0 | N S | 8,7 20,3 | N S |
| 47 | [structure] 92% M 344 | [structure with OCH₃-phenyl, S, P, OC₂H₅, Na—S] | [structure CH₃, N—N, O, CH₂Cl] | $n_D^{20} = 1.578$ | 9,0 8,2 | P N | 8,7 8,4 | P N |
| 48 | [structure] 94% MW 266 | [structure CH₃P, S, SNa, O—C₃H₇(n)] | [structure CH₃, N—N, O, CH₂Cl] | 1.5446 | 10,5 11,6 | N P | 10,8 11,6 | N P |
| 49 | [structure] 89% MW 294 | [structure CH₃P, S, SNa, O—C₅H₁₁(n)] | [structure CH₃, N—N, O, CH₂Cl] | 1.5328 | 9,5 10,5 | N P | 9,6 10,6 | N P |
| 50 | [structure] 88% MW 264 | [structure CH₃P, S, SNa, OCH₂CH=CH₂] | [structure CH₃, N—N, O, CH₂Cl] | 1.5473 | 10,4 11,6 | N P | 10,9 11,6 | N P |
| 51 | [structure] 72% MW 262 | [structure CH₃P, S, SNa, OCH₂C≡CH] | [structure CH₃, N—N, O, CH₂Cl] | 1.5737 | 10,6 11,4 | N P | 10,6 11,4 | N P |
| 52 | [structure] 85% MW 266 | [structure CH₃P, S, SNa, O—CH(CH₃)₂] | [structure CH₃, N—N, O, CH₂Cl] | 1.5418 | 10,5 11,6 | N P | 10,5 11,8 | N P |

TABLE IV-continued

| Ex. No. | Reaction product/yield/MW % of theory | | reactants | | phys. data | analysis in % calc. | | analysis in % found | |
|---|---|---|---|---|---|---|---|---|---|
| | | | III | IV | | | | | |
| 53 | (structure with O-C₁₂H₂₅) 94% MW 392 | | CH₃P(S)(SNa)(O-C₁₂H₂₅) | oxadiazole-CH₂Cl | 1.5082 | N 7,1 | P 7,9 | N 7,4 | P 7,6 |
| 54 | (O-C₂H₄OCH₃) 86% MW 282 | | CH₃P(S)(SNa)(O-C₂H₄OCH₃) | oxadiazole-CH₂Cl | 1.5479 | N 9,9 | P 11,0 | N 10,4 | P 10,9 |
| 55 | (O-C₂H₄CN) 80% MW 277 | | CH₃P(S)(SNa)(O-C₂H₄CN) | oxadiazole-CH₂Cl | 1.5312 | N 15,2 | P 11,2 | N 15,5 | P 10,8 |
| 56 | (O-C₂H₄SC₃H₇) 86% MW 326 | | CH₃P(S)(SNa)(O-C₂H₄SC₃H₇) | oxadiazole-CH₂Cl | 1.5658 | N 8,6 | P 9,5 | N 8,8 | P 9,3 |
| 57 | (O-C₃H₇(n)) 89% MW 280 | | C₂H₅P(S)(SNa)(O-C₃H₇(n)) | oxadiazole-CH₂Cl | 1.5369 | N 10,1 | P 11,1 | N 9,8 | P 10,9 |
| 58 | (O-CH(CH₃)₂) 88% MW 280 | | C₂H₅P(S)(NaSP)(O-CH(CH₃)₂) | oxadiazole-CH₂Cl | 1.5345 | N 10,0 | P 11,1 | N 9,9 | P 11,1 |
| 59 | (O-C₄H₉(n)) 85% MW 294 | | C₂H₅P(S)(NaSP)(O-C₄H₉(n)) | oxadiazole-CH₂Cl | 1.5329 | N 9,5 | P 10,5 | N 9,7 | P 10,5 |

TABLE IV-continued

| Ex. No. | Reaction product/yield/MW % of theory | reactants | | phys. data | analysis in % calc. | | analysis in % found |
|---|---|---|---|---|---|---|---|
| | | III | IV | | | | |
| 60 | [structure with N-N, CH₃, O, CH₂-S-P(=S)(C₂H₅)(O-C₄H₉(sec.))] MW 294, 86% | NaSP(=S)(C₂H₅)(O-C₄H₉(sec.)) | [structure with N-N, CH₃, O, CH₂Cl] | 1.5321 | 9,5 10,5 | N P | 9,8 10,3 |
| 61 | [analogous structure O-C₄H₉(iso)] MW 294, 92% | NaSP(=S)(C₂H₅)(O-C₄H₉(iso)) | [same] | 1.5292 | 9,5 10,5 | N P | 9,5 10,3 |
| 62 | [analogous O-C₅H₁₁(n)] MW 308, 82% | NaSP(=S)(C₂H₅)(O-C₅H₁₁(n)) | [same] | 1.5292 | 9,1 10,1 | N P | 9,1 9,7 |
| 63 | [analogous O-C₁₂H₂₅] MW 406, 95% | NaSP(=S)(C₂H₅)(O-C₁₂H₂₅) | [same] | 1.5072 | 6,9 7,7 | N P | 7,2 7,4 |
| 64 | [analogous O-CH₂CH=CH₃] MW 278, 89% | NaSP(=S)(C₂H₅)(O-CH₂CH=CH₃) | [same] | 1.5511 | 9,6 10,6 | N P | 9,8 10,3 |
| 65 | [analogous O-CH₂-C≡CH] MW 286, 84% | NaSP(=S)(C₂H₅)(O-CH₂-C≡CH) | [same] | 1.5593 | 9,8 10,8 | N P | 9,9 10,8 |
| 66 | [analogous O-C₂H₄CN] MW 291, 86% | NaSP(=S)(C₂H₅)(O-C₂H₄CN) | [same] | 1.5608 | 14,4 10,6 | N P | 14,4 10,5 |

TABLE IV-continued

| Ex. No. | Reaction product/yield/MW % of theory | reactants III | IV | phys. data | analysis in % calc. | analysis in % found |
|---|---|---|---|---|---|---|
| 67 | [structure] 85% MW 312 | [structure with C₂H₅, O-C₂H₄SCH₃] | [structure with CH₃, CH₂Cl] | 1.5729 | N 9,0 P 30,7 | N 9,4 P 29,6 |
| 68 | [structure] 8,8% MW 328 | [structure with C₂H₅, O-CH₂-phenyl] | [structure with CH₃, CH₂Cl] | 1.5839 | N 8,5 P 9,5 | N 8,7 P 9,0 |
| 69 | [structure] 93% MW 308 | [structure with C₃H₇, O-C₄H₉(sec)] | [structure with CH₃, CH₂Cl] | 1.5278 | N 9,1 P 10,1 | N 9,1 P 9,7 |
| 70 | [structure] 91% MW 308 | [structure with C₃H₇, O-C₄H₉(iso)] | [structure with CH₃, CH₂Cl] | 1.5277 | N 9,1 P 10,1 | N 9,5 P 9,9 |
| 71 | [structure] 87% MW 310 | [structure with C₃H₇, O-C₄H₉OCH₃] | [structure with CH₃, CH₂Cl] | 1.5332 | N 8,7 P 10,0 | N 9,2 P 9,9 |
| 72 | [structure] 90% MW 322 | [structure with C₃H₇, O-C₅H₁₁(n)] | [structure with CH₃, CH₂Cl] | 1.5246 | N 8,4 P 9,6 | N 8,7 P 9,6 |
| 73 | [structure] 75% MW 420 | [structure with C₃H₇, O-C₁₂H₂₅] | [structure with CH₃, CH₂Cl] | 1.5512 | N 6,7 P 7,4 | N 7,0 P 7,4 |

TABLE IV-continued

| Ex. No. | Reaction product/yield/MW % of theory | reactants III | IV | phys. data | analysis in % calc. | | analysis in % found |
|---|---|---|---|---|---|---|---|
| 74 | [structure with CH₃, N-N, O, CH₂-S-P(=S)(C₃H₇)(OCH₂-phenyl)] 82% MW 342 | NaSP(=S)(C₃H₇)(OCH₂-phenyl) | [structure with CH₃, N-N, O, CH₂Cl] | 1.5762 | 8,2 9,1 | N P | 8,6 8,8 |
| 75 | [structure with CH₃, N-N, O, CH₂-S-P(=S)(C₃H₇)(O-phenyl-H)] 75% MW 334 | NaSP(=S)(C₃H₇)(O-phenyl-H) | [structure with CH₃, N-N, O, CH₂Cl] | 1.5423 | 8,4 9,0 | N P | 8,0 9,2 |
| 76 | [structure with CH₃, N-N, O, CH₂-S-P(=S)(C₂H₅)(O-phenyl-H)] 84% MW 320 | NaSP(=S)(C₂H₅)(O-phenyl-H) | [structure with CH₃, N-N, O, CH₂Cl] | 1.5469 | 8,7 9,7 | N P | 8,0 9,5 |
| 77 | [structure with CH₃, N-N, O, CH₂-S-P(=S)(C₂H₅)(O-C₂H₄OCH₃)] 89% MW 296 | NaSP(=S)(C₂H₅)(O-C₂H₄OCH₃) | [structure with CH₃, N-N, O, CH₂Cl] | 1.5401 | 9,5 10,5 | N P | 9,7 10,1 |
| 78 | [structure with CH₃, N-N, O, CH₂-S-P(=S)(C₃H₇)(O-C₃H₇(n))] 89% MW 294 | NaSP(=S)(C₃H₇)(O-C₃H₇(n)) | [structure with CH₃, N-N, O, CH₂Cl] | 1.5318 | 9,6 10,5 | N P | 9,5 10,2 |
| 79 | [structure with CH₃, N-N, O, CH₂-S-P(=S)(C₃H₇)(O-CH(CH₃)₂)] 89% MW 294 | NaSP(=S)(C₃H₇)(O-CH(CH₃)₂) | [structure with CH₃, N-N, O, CH₂Cl] | 1.5290 | 9,6 10,5 | N P | 9,3 10,2 |
| 80 | [structure with CH₃, N-N, O, CH₂-S-P(=S)(C₃H₇)(O-CH₂CH=CH₂)] 90% MW 292 | NaSP(=S)(C₃H₇)(O-CH₂CH=CH₂) | [structure with CH₃, N-N, O, CH₂Cl] | 1.5442 | 9,6 10,6 | N P | 9,8 10,3 |

TABLE IV-continued

| Ex. No. | Reaction product/yield/MW % of theory | reactants III | IV | phys. data | analysis in % calc. | analysis in % found |
|---|---|---|---|---|---|---|
| 81 | [structure] 90% MW 290 | [structure] | [structure] | 1.5532 | N 9,7 P 10,6 | N 9,3 P 10,2 |
| 82 | [structure] 94% MW 308 | [structure] | [structure] | 1.5278 | N 9,1 P 10,1 | N 9,1 P 9,7 |
| 83 | [structure] 79% MW 305 | [structure] | [structure] | 1.5471 | N 13,8 P 10,1 | N 13,6 P 9,9 |
| 84 | [structure] 98% MW 328 | [structure] | [structure] | 1.5869 | N 8,5 P 9,4 | N 8,8 P 9,1 |
| 85 | [structure] | [structure] | [structure] | 1.543 | N 10,5 P 11,65 | N 10,6 P 11,8 |
| 86 | [structure] | [structure] | [structure] | 1.536 | N 10,0 P 11,1 | N 9,9 P 10,8 |
| 87 | [structure] | [structure] | [structure] | 1.507 | N 9,1 P 10,0 | N 9,1 P 9,5 |
| 88 | [structure] | [structure] | [structure] | 1.510 | N 9,5 P 10,5 | N 9,6 P 10,9 |

TABLE IV-continued

| Ex. No. | Reaction product/yield/MW % of theory | reactants | | phys. data | analysis in % calc. | analysis in % found |
|---|---|---|---|---|---|---|
| | | III | IV | | | |
| 89 | (CH₃)₂CH–N=N–O–C(=O)–CH₂–S–P(=S)(C₂H₅)(OCH(CH₃)₂) | NaSP(=S)(C₂H₅)(OCH(CH₃)₂) | (CH₃)₂CH–N=N–O–C(=O)–CH₂Cl | 1.516 | N 9,1<br>P 10,05 | N 9,4<br>P 10,3 |
| 90 | (CH₃)₂CH–N=N–O–C(=O)–CH₂–S–P(=S)(C₂H₅)(O–C₄H₉(n)) | NaSP(=S)(C₂H₅)(O–C₄H₉(n)) | (CH₃)₂CH–N=N–O–C(=O)–CH₂Cl | 1.507 | N 8,7<br>P 9,6 | N 8,6<br>P 9,7 |
| 91 | (CH₃)₂CH–N=N–O–C(=O)–CH₂–S–P(=S)(C₃H₇(n))(OC₂H₅) | NaSP(=S)(C₃H₇(n))(OC₂H₅) | (CH₃)₂CH–N=N–O–C(=O)–CH₂Cl | 1.518 | N 9,1<br>P 10,05 | N 9,3<br>P 9,7 |
| 92 | (CH₃)₂CH–N=N–O–C(=O)–CH₂–S–P(=S)(C₃H₇(n))(O–C₃H₇(n)) | NaSP(=S)(C₃H₇(n))(O–C₃H₇(n)) | (CH₃)₂CH–N=N–O–C(=O)–CH₂Cl | 1.520 | N 8,7<br>P 9,6 | N<br>P |
| 93 | (CH₃)₂CH–N=N–O–C(=O)–CH₂–S–P(=S)(C₄H₉(n))(OCH₃) | NaSP(=S)(C₄H₉(n))(OCH₃) | (CH₃)₂CH–N=N–O–C(=O)–CH₂Cl | 1.513 | N 9,1<br>P 10,05 | N 9,4<br>P 10,3 |
| 94 | (CH₃)₂CH–N=N–O–C(=O)–CH₂–S–P(=S)(C₄H₉(i))(OCH₃) | NaSP(=S)(C₄H₉(i))(OCH₃) | (CH₃)₂CH–N=N–O–C(=O)–CH₂Cl | 1.514 | N 9,1<br>P 10,05 | N 9,2<br>P 10,0 |

EXAMPLES OF APPLICATION

EXAMPLE I

Bean plants being heavily infested with spider mites (Tetranychus urticae) were drip-sprayed with the aqueous dilution of an emulsdion concentrate containing 0.003 wt.% of the active compound according to Example 25. Subsequently, the plants were placed in a greenhouse at 20° C. Upon checking by micorscope 8 days after the spraying, all the mobile and immobile phases of the mite population were destroyed.

Upon testing in the same way the compounds according to Examples 24, 32, 26, 4, 5, 31, 3, 40, 38, 35, 39, 34 and 2 proved to be equally efficient.

EXAMPLE II

Potted young apple trees being heavily infested by a strain of fruit-tree red spider (Metatetranychus ulmi) resistent to phosphoric acid esters were sprayed to dripping wetness with an aqueous dilution of an emulsion concentrate containing 0.0125 wt% of the active compound according to Example 31, and subsequently placed in a green-house at 20° C. Upon checking by microscope 8 days after spraying, all the mobile and immobile phases of the fruit-tree red spider had been destroyed.

Upon testing in the same way the compounds according to Examples 24, 26 3 proved to be equally efficient.

However, the following phosphoric acid esters, even though applied in high concentrations of the active agents, were entirely inefficient:

| phenkaptone | 0.025 wt. % conc. | no effect |
|---|---|---|
| demeton-S-methyl | 0.05 wt. % conc. | no effect |
| dimethoate | 0.05 wt. % conc. | no effect |

EXAMPLE III

The systemic properties of the active compounds were proved by the following test arrangement:

The roots of broad beans (Vicia faba), the above-ground growing parts of which were being sucked by 200–300 aphids, were wrapped in a plastics bag so as to eliminate the gas phase effect. 10 ml. of an aqueous dilution of an emulsion concentrate were then dispersed in the root area of the plants, the concentrate containing 0.125 mg of the active compound according to Example 25. The plants were placed in a greenhouse at 20° C. The active agent was rapidly absorbed by the roots and carried to the above-ground growing parts of the plants.

Upon checking 3 days after the application, all the aphids had been destroyed.

Upon testing in the same way, the active compounds according to Examples 24, 26, 4, 31, and 3 proved to be equally efficient.

EXAMPLE IV

By a similar method and at a similar concentration as described for Example III broad beans being heavily infested by spider mites (Tetranychus urticae) were treated.

Upon checking 8 days after having applied the active compound according to Example 25, all the mobile and immobile phases were destroyed. The same good effect was obtained by using the compounds according to Example 24, 26 and 31 in the test arrangements as described.

EXAMPLE V

Potted young cotton plants (Gossypium spec.) being infested with African cotton stainers (Dysdercus fasciatus) (5 plants each infested with 20 insects) were sprayed to dripping wetness with an aqueous dilution of a wettable powder concentrate containing 0.006 wt.% of the active compound according to Example 4. subsequently, the plants with the cotton stainers were put in cylindrical gaze cages and placed in a greenhouse at 22° C.

Upon checking after 48 hours, all the cotton stainers had been destroyed.

The same testing method proved the compounds according to Examples 24, 25, 26, 31, 3, 40, 33, 37, 35, 39, 36, 43, 34, 42, 1 and 2 to be equally efficient.

EXAMPLE VI

Larvae (3rd phase) of the Asian cotton moth (Prodenia litura) and cotton leaves were sprayed with a determined quantity of an aqueous dilution of an emulsion concentrate containing the active compound according to Example 35 and subsequently placed in the laboratory at 22° C in open vessels (5 vessels with 10 larvae each).

A concentration of 0.0024 mg/cm$^2$ of the active agent was sufficient for destroying all the test insects within the specified lapse of time.

When using the same test arrangement, the active compounds according to Example 24, 25, 26 and 31 were equally efficient.

EXAMPLE VII

Larvae (4th phase) of the Mexican bean beetle (*Epilachna varivestis*) and leaves of dwarf bush beans (*Phaseolus vulgaris*) were sprayed with a determined quantity (corresponding to an applied quantity of 600 ltr/ha in the field) of the aqueous dilution of an emulsion concentrate containing the active compound according to Example 4, subsequently placed in the laboratory at 22° C in open vessels. 48 hours later the mortality rate was determined (5 vessels each containing 10 larvae).

The concentration of 0.003 mg/cm$^2$ of active agent was sufficient for destroying the larvae by 100%.

When using the compounds according to Examples 25, 26, 31, 33, 37, 38, 36 and 2 in the same test arrangement, the results were equally good.

EXAMPLE VIII

In earth-filled rectangular plates (40 × 60 × 10 cms) seeds of broad beans (Vicia faba) were placed in drills; simultaneously a granular formulation containing the active compound according to Example 35 at the rate of 5 wt.% — corresponding to an applied quantity of 1.5 kg of active agent per hectare — was dispersed in the same drills which were then covered with earth. Subsequently, these plates (8 series) went to the greenhouse at 20° C. For the test period the earth was kept slightly humid.

After the germination of the seed and the plants having reached 10 to 15 cms height (= 14 days), same were heavily infested with spider mites (Tetranychus urticae).

Another week later (= 3 weeks after sowing) checking proved that the spider mites which had crawled onto the plants, had been destroyed and that no population had been formed.

Further infections with spider mites in weekly intervals proved upon checking that in each case the spider mites were destroyed for a period of up to 10 weeks after the infection.

On control plants infested simultaneously and left without treatment, the spider mites spread heavily and destroyed the plants.

Upon using the active compounds of Examples 34, 39, 25 and 24 for the same test arrangement, same proved to be equally efficient.

Granules containing 10 wt% of "Carbofurane" did not produce any effect, though it was applied in twice the amount, of 3 kg of active agent per hectare, and while using the same test arrangement.

We claim:

1. A compound of the formula

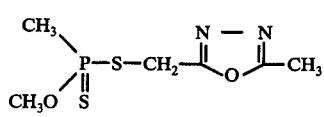

2. A compound of the formula

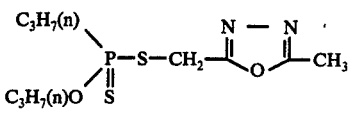

3. A compound of the formula

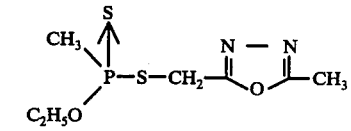

4. A compound of the formula

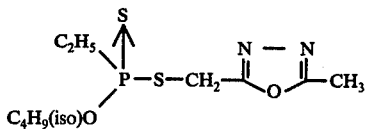

* * * * *